| (12) | United States Patent | (10) Patent No.: | US 11,963,987 B2 |
|---|---|---|---|
| | Ho et al. | (45) Date of Patent: | Apr. 23, 2024 |

(54) HEPATOPROTECTION FOOD COMPOSITION AND PHARMACEUTICAL COMPOSITION WITH STRAINS OF LACTIC ACID BACTERIA

(71) Applicant: GLAC BIOTECH CO., LTD., Tainan (TW)

(72) Inventors: Hsieh-Hsun Ho, Tainan (TW); Yi Wei Kuo, Tainan (TW); Jui-Fen Chen, Tainan (TW); Ching-Wei Chen, Tainan (TW)

(73) Assignee: GLAC BIOTECH CO., LTD., Tainan (TW)

(*) Notice: Subject to any disclaimer, the term of this patent is extended or adjusted under 35 U.S.C. 154(b) by 313 days.

(21) Appl. No.: 17/320,820

(22) Filed: May 14, 2021

(65) Prior Publication Data

US 2021/0268048 A1 Sep. 2, 2021

Related U.S. Application Data

(63) Continuation-in-part of application No. 16/389,297, filed on Apr. 19, 2019, now abandoned.

(51) Int. Cl.
*A61K 35/747* (2015.01)
*A23L 33/135* (2016.01)

(52) U.S. Cl.
CPC .......... *A61K 35/747* (2013.01); *A23L 33/135* (2016.08)

(58) Field of Classification Search
None
See application file for complete search history.

(56) References Cited

U.S. PATENT DOCUMENTS

2016/0113975 A1 4/2016 Chen et al.

FOREIGN PATENT DOCUMENTS

| CN | 1853508 A | * | 11/2006 | ............... A23L 2/52 |
| CN | 107496850 B | * | 8/2018 | ............... A23L 11/05 |

OTHER PUBLICATIONS

Adawi et al., Hepatol., 25:642-647 (1997) (Year: 1997).*
Cederbaum et al., Arch. Toxicol., 83:519-548 (2009) (Year: 2009).*
Chuang et al., Molecules, 21(1456):1-11 (2016) (Year: 2016).*
Dey et al., Hepatol., 43:S63-S74 (2006) (Year: 2006).*
Fernandez-Checa et al., Alcohol Health Res. World, 21(4):321-324 (1997) (Year: 1997).*
Segawa et al., Int. J. Food Microbiol., 128:371-377 (2008) (Year: 2008).*
Tian et al., J. Microbiol., 53(12):856-863 (2015) (Year: 2015).*
Zhao et al., J. Funct. Foods, 35:97-104 (2017) (Year: 2017).*
Huang et al. (PloS ONE, 12(1): e0170109 (2017) (Year: 2017).*
Chen et al., Int. J. Mol. Sci., 19(2212):1-12 (2018) (Year: 2018).*
Hsieh et al., Nutr. Metab., 10(35):1-14 (2013) (Year: 2013).*

* cited by examiner

*Primary Examiner* — Thomas J. Visone
(74) *Attorney, Agent, or Firm* — Locke Lord LLP; Tim Tingkang Xia, Esq.

(57) ABSTRACT

At least one isolated lactic acid bacteria strains selected from the following: TSP05 (*Lactobacillus plantarum*), TSF331 (*Lactobacillus fermentum*) and TSR332 (*Lactobacillus reuteri*) is provided. The above-mentioned active or inactive lactic acid bacteria strains have a function of hepatoprotection and is used in a form of a food composition or a pharmaceutical composition.

6 Claims, 4 Drawing Sheets

HEPATOPROTECTION FOOD COMPOSITION AND PHARMACEUTICAL COMPOSITION WITH STRAINS OF LACTIC ACID BACTERIA

CROSS-REFERENCE TO RELATED APPLICATIONS

This is a continuation-in-part Application of U.S. patent application Ser. No. 16/389,297, filed Apr. 19, 2019. This continuation-in-part Application claims the benefit of the U.S. patent application Ser. No. 16/389,297.

BACKGROUND OF THE INVENTION

1. Field of the Invention

The present invention relates to a food composition and a pharmaceutical composition, particularly to a hepatoprotection food composition and pharmaceutical composition with strains of lactic acid bacteria.

2. Description of the Prior Art

The liver is the largest organ in the human body, performing very important functions, including 1. Blood circulation: circulating blood from the hepatic artery to the whole body, involving in the immunological mechanism through the reticuloendothelial system thereof, storing blood and regulating blood volume; 2. Excretion: generating bile to the intestines, wherein the bilirubin conjugates, cholesterol and cholic acid, which are excreted by the liver, together with the bile to form bile salts, and removing the materials that the liver cells separate from the blood, such as heavy metals, bromsulphalein, and alkaline phosphatase etc.; 3. Metabolism: involving in the metabolism of carbohydrates, proteins, lipids, minerals and vitamins, and generating heat; 4. Protection and detoxification: removing the foreign bodies in the blood through endocytosis of Kupffer cells, lowering the toxicity of poisonous materials through bonding, methylation, oxidation and reduction, driving out the poisonous materials through the excretion system, and removing ammonia from the blood, especially the ammonia from the portal vein; 5. Hematopoiesis and blood coagulation: forming blood in the embryonic stage, also forming blood in the adulthood in some special conditions, generating coagulants, such as fibrinogen, prothrombin and heparin, and destroying aged red blood cells. Therefore, it is very important for a person to maintain the normal functions of the liver.

Ethanol (alcohol) is an important hepatitis-inducing factor. Long-term alcoholism may lead to alcoholic hepatitis. The symptoms of alcoholic hepatitis include discomfort, hepatomegaly, ascites, and higher values of liver function indexes. Slighter alcoholic hepatitis only leads to higher values of liver function indexes. More severe alcoholic hepatitis shows symptoms of severe liver inflammation, jaundice, prolonged prothrombin time, and liver function failure. The most severe alcoholic hepatitis cases can be unconscious, accompanied by an increase in bilirubin values and prolonged prothrombin time. Severe alcoholic hepatitis has a mortality rate as high as 50% within 30 days from the appearance of these symptoms.

The anatomy of the non-alcoholic fatty liver disease (NAFLD) is very similar to that of alcoholic hepatitis (lipid droplets and inflammatory cells). However, the patients of NAFLD are free of alcoholism. A similar but moderate disease is steatosis hepatis, also called the fatty liver. 80% of the patients suffering obesity also suffer steatosis hepatis. Lipid droplets appear all over in the anatomy of the liver of the patient suffering steatosis hepatis. However, no inflammation appears in the anatomy of the liver of the patient suffering steatosis hepatis. Steatosis hepatis may further evolve into hepatitis, hepatic cirrhosis, or even hepatoma.

So far, only few strains of lactic acid bacteria have been experimentally confirmed to have the effect of protecting livers. The functionality of lactic acid bacteria to health is not based on the species of bacteria but dependent on the specificities of strains. The strains favorable to health are called the probiotics (Guidelines for the evaluation of probiotics in food; Report of joint FAO/WHO working group on drafting guidelines for the evaluation of probiotics in food; London Ontario, Canada April 30 and May 1, 2002:1-7).

Accordingly, it is an urgency to develop a nutrient that is safe and can be used for a long time to protect livers. In general, lactic acid bacteria are safe for human beings. Therefore, finding out lactic acid bacteria strains and its inactive strains able to protect livers becomes a target the manufacturers are eager to achieve.

SUMMARY OF THE INVENTION

The present invention provides a food composition and pharmaceutical composition with strains of active or inactive lactic acid bacteria, which can protect livers and relieve liver inflammation and fatty livers.

In one embodiment, the present invention provides a food composition with strains of lactic acid bacteria, which comprises lactic acid bacteria strains able to prevent livers from damage caused by oxidative stress, and a physiologically-acceptable excipient, diluent or carrier. The lactic acid bacteria strain comprises at least one isolated lactic acid bacteria strain of a TSP05 strain of *Lactobacillus plantarum* (CGMCC No. 16710), a TSF331 strain of *Lactobacillus fermentum* (CGMCC No. 15527), and a TSR332 strain of *Lactobacillus reuteri* (CGMCC No. 15528). The abovementioned lactic acid bacteria strains are deposited in China General Microbiological Culture Collection Center (CGMCC).

In another embodiment, the present invention provides a pharmaceutical composition with strains of lactic acid bacteria, which comprises lactic acid bacteria strains able to prevent livers from damage caused by oxidative stress, and a pharmaceutically-acceptable excipient, diluent or carrier. The lactic acid bacteria strain comprises at least one isolated lactic acid bacteria strain of a TSP05 strain of *Lactobacillus plantarum* (CGMCC No. 16710), a TSF331 strain of *Lactobacillus fermentum* (CGMCC No. 15527), and a TSR332 strain of *Lactobacillus reuteri* (CGMCC No. 15528). The abovementioned lactic acid bacteria strains are deposited in China General Microbiological Culture Collection Center (CGMCC).

In yet another embodiment, the present invention provides a method for preventing livers from damage caused by oxidative stress, comprising administering a composition with lactic acid bacteria strains to a subject, wherein the composition comprises lactic acid bacteria strains able to prevent livers from damage caused by oxidative stress, and a physiologically or pharmaceutically-acceptable excipient, diluent or carrier. The lactic acid bacteria strain comprises at least one isolated lactic acid bacteria strain of a TSP05 strain of *Lactobacillus plantarum* (CGMCC No. 16710), a TSF331 strain of *Lactobacillus fermentum* (CGMCC No. 15527), and a TSR332 strain of *Lactobacillus reuteri* (CGMCC No.

15528). The abovementioned lactic acid bacteria strains are deposited in China General Microbiological Culture Collection Center (CGMCC).

Below, embodiments are described in detail in cooperation with the attached drawings to make easily understood the objectives, technical contents, characteristics and accomplishments of the present invention.

BRIEF DESCRIPTION OF THE DRAWINGS

FIG. 1 shows the alanine aminotransferase (ALT) activities in the serum of the groups of mice fed with the lactic acid bacteria strains of the present invention in animal experiments, wherein the symbol OW represents at initial stage of the experiment; the symbol 2W and 4W respectively represents in the second week and the fourth week of the experiment; the symbol Alcohol+Mix-LAB represents the mice are fed with LIEBER-DECARLI REGULAR LIQUID DIET ETHANOL and the TSP05 strain of *Lactobacillus plantarum*, the TSF331 strain of *Lactobacillus fermentum* and the TSR332 strain of *Lactobacillus reuteri*; and the symbol Mix-LAB represents the mice are fed with LIEBER-DECARLI REGULAR LIQUID DIET CONTROL and the TSP05 strain of *Lactobacillus plantarum*, the TSF331 strain of *Lactobacillus fermentum* and the TSR332 strain of *Lactobacillus reuteri*;

FIG. 2 shows the aspartate transaminase (AST) activities in the serum of the groups of mice fed with the lactic acid bacteria strains of the present invention in animal experiments, wherein the symbol OW represents at initial stage of the experiment; the symbol 2W and 4W respectively represents in the second week and the fourth week of the experiment; the symbol Alcohol+Mix-LAB represents the mice are fed with LIEBER-DECARLI REGULAR LIQUID DIET ETHANOL and the TSP05 strain of *Lactobacillus plantarum*, the TSF331 strain of *Lactobacillus fermentum* and the TSR332 strain of *Lactobacillus reuteri*; and the symbol Mix-LAB represents the mice are fed with LIEBER-DECARLI REGULAR LIQUID DIET CONTROL and the TSP05 strain of *Lactobacillus plantarum*, the TSF331 strain of *Lactobacillus fermentum* and the TSR332 strain of *Lactobacillus reuteri*;

FIG. 3 shows the triacylglycerol concentrations in the serum of the groups of mice fed with the lactic acid bacteria strains of the present invention in animal experiments, wherein the symbol OW represents at initial stage of the experiment; the symbol 2W and 4W respectively represents in the second week and the fourth week of the experiment; the symbol Alcohol+Mix-LAB represents the mice are fed with LIEBER-DECARLI REGULAR LIQUID DIET ETHANOL and the TSP05 strain of *Lactobacillus plantarum*, the TSF331 strain of *Lactobacillus fermentum* and the TSR332 strain of *Lactobacillus reuteri*; and the symbol Mix-LAB represents the mice are fed with LIEBER-DECARLI REGULAR LIQUID DIET CONTROL and the TSP05 strain of *Lactobacillus plantarum*, the TSF331 strain of *Lactobacillus fermentum* and the TSR332 strain of *Lactobacillus reuteri*;

FIG. 4 shows the total cholesterol concentrations in the serum of the groups of mice fed with the lactic acid bacteria strains of the present invention in the animal experiments, wherein the symbol OW represents at initial stage of the experiment; the symbol 2W and 4W respectively represents in the second week and the fourth week of the experiment; the symbol Alcohol+Mix-LAB represents the mice are fed with LIEBER-DECARLI REGULAR LIQUID DIET ETHANOL and the TSP05 strain of *Lactobacillus plantarum*, the TSF331 strain of *Lactobacillus fermentum* and the TSR332 strain of *Lactobacillus reuteri*; and the symbol Mix-LAB represents the mice are fed with LIEBER-DECARLI REGULAR LIQUID DIET CONTROL and the TSP05 strain of *Lactobacillus plantarum*, the TSF331 strain of *Lactobacillus fermentum* and the TSR332 strain of *Lactobacillus reuteri*;

DESCRIPTION OF THE PREFERRED EMBODIMENTS

The present invention will be described in detail with embodiments and attached drawings below. However, these embodiments are only to exemplify the present invention but not to limit the scope of the present invention. In addition to the embodiments described in the specification, the present invention also applies to other embodiments. Further, any modification, variation, or substitution, which can be easily made by the persons skilled in the art according to the embodiment of the present invention, is to be also included within the scope of the present invention, which is based on the claims stated below. Although many special details are provided herein to make the readers more fully understand the present invention, the present invention can still be practiced under a condition that these special details are partially or completely omitted. Besides, the elements or steps, which are well known by the persons skilled in the art, are not described herein lest the present invention be limited unnecessarily. Similar or identical elements are denoted with similar or identical symbols in the drawings. It should be noted: the drawings are only to depict the present invention schematically but not to show the real dimensions or quantities of the present invention. Besides, matterless details are not necessarily depicted in the drawings to achieve conciseness of the drawings.

The freeze-dried cultures of the strains of lactic acid bacteria mentioned in the specification are deposited in China General Microbiological Culture Collection Center (CGMCC) of Chinese Academy of Sciences (NO.1 West Beichen Road, Chaoyang District, Beijing 100101, China). The details thereof are listed in Table. 1.

TABLE 1

Data of Deposited Strains of Lactic Acid Bacteria

| Strain | Specie | Deposition No. | Deposition Date |
|---|---|---|---|
| TSP05 | Lactobacillus plantarum | CGMCC No. 16710 | Nov. 5, 2018 |
| TSF331 | Lactobacillus fermentum | CGMCC No. 15527 | Mar. 29, 2018 |
| TSR332 | Lactobacillus reuteri | CGMCC No. 15528 | Mar. 29, 2018 |

The three lactic acid bacteria strains listed in Table.1, which are respectively the TSP05 strain of *Lactobacillus plantarum*, the TSF331 strain of *Lactobacillus fermentum* and the TSR332 strain of *Lactobacillus reuteri*, were found to be able to protect livers and prevent from liver inflammation.

The present invention provides a food composition, which comprises lactic acid bacteria strains able to protect livers, and a physiologically-acceptable excipient, diluent or carrier. The present invention also provides a pharmaceutical composition, which comprises lactic acid bacteria strains able to protect livers, and a pharmaceutically-acceptable excipient, diluent or carrier. The lactic acid bacteria strain is at least one isolated lactic acid bacteria strain selected from a group including a TSP05 strain of *Lactobacillus plantarum* (CGMCC No. 16710), a TSF331 strain of *Lactobacillus fermentum* (CGMCC No. 15527), and a TSR332 strain of *Lactobacillus reuteri* (CGMCC No. 15528). The abovementioned lactic acid bacteria strains are deposited in China General Microbiological Culture Collection Center (CGMCC). In one embodiment, the lactic acid bacteria strains are active or inactivated strains. The term "active strain" means the lactic acid bacteria strains of the present invention can proliferate. The term "inactivated strain" means the lactic acid bacteria strains of the present invention cannot proliferate after heating or other appropriate treatments.

In the embodiment of the food composition, the physiologically-acceptable excipient, diluent or carrier may be a food. For example, the food may be but is not limited to be dairy food, tea, coffee, chewing gum, a tooth-cleaning candy (such as an oral strip, a chewable tablet, or, jelly sweets) or a combination thereof. The dairy food may be fermented milk, yoghurt, cheese, or powdered milk etc. The pharmaceutical composition may be in form of an oral dosage, such as a tablet, a capsule, a solution, or a powder.

In the embodiments of the food composition and the pharmaceutical composition, the number of the lactic acid bacteria strains may be over 106 CFU (Colony-Forming Unit), preferably $10^{10}$ CFU.

It should be explained: documents point out that the lactic acid bacteria strains belonging to an identical specie are not all favorable for hepatoprotection. For example, Xingrong Zhao, et al. used high fat diet to generate obese mice and used the obese mice to investigate the effect of lactic acid bacteria strains on obesity and fatty livers induced by high fat diet (Xingrong Zhao et al., (2012). "The obesity and fatty liver are reduced by plant-derived *Pediococcus pentosaceus* LP28 in high fat diet-induced obese mice". PLoS ONE Volume 7, Issue 2, Article ID: e30696. https://doi:10.1371/journal.pone.0030696). The experimental result shows that only the LP28 strain of *Pediococcus pentosaceus* can inhibit rising of body weight and reduce triacylglycerol and cholesterol in livers and that the SN13T strain of *Lactobacillus plantarum* and the heat killed LP28 strain do not have the same effect. Yi Qiao et al. used high fat diet to generate obese mice and used the obese mice to investigate the effect of the L3 strain and L10 strain of *Lactobacillus reuteri* on inflammation and fat accumulation (Qiao et al., (2015). "Effects of different *Lactobacillus reuteri* on inflammatory and fat storage in high-fat diet-induced obesity mice model". Journal of Functional Foods, Volume 14, Pages 424-434). The experimental result shows that only the L3 strain can improve liver hypertrophy and hepatic steatosis and that the L10 strain does not have the same effect. Therefore, the present invention does not extensively claim all lactic acid bacteria strains but only claims the three strains deposited in China General Microbiological Culture Collection Center (CGMCC), which are respectively the TSP05 strain of *Lactobacillus plantarum* (CGMCC No. 16710), the TSF331 strain of *Lactobacillus fermentum* (CGMCC No. 15527), and the TSR332 strain of *Lactobacillus reuteri* (CGMCC No. 15528).

Example I: Morphologies and General Properties of the Strains of Lactic Acid Bacteria Able to Protect Livers The taxonomic characteristics of the strains are identified with the 16S rDNA sequencing analysis and the API bacterial identification system. The morphologies and general properties of the strains are listed in Table.2.

TABLE 2

Morphologies and General Properties of Lactic Acid Bacteria Strains of the Present Invention

| Strain | Morphology and characteristics |
|---|---|
| TSP05 strain of *Lactobacillus plantarum* | 1. While TSP05 strain is cultured in the MRS medium, the colony thereof has a shape of a solid circle and a color of white, the bodies of the bacteria each have a shape of a short rod, and the ends of the body are circular-shaped. They often appear in single bodies.<br>2. They are gram-positive bacilli, unlikely to generate spores, free of catalase, oxidase and motility, able to grow in aerobic and anaerobic environments, most suitable to grow at a temperature of 37 ± 1° C.. They belong to a facultative heterofermentative strains and do not generate gas in glucose metabolism. |
| TSF331 strain of *Lactobacillus fermentum* | 1. While TSF331 strain is cultured in the MRS medium, the colony thereof has a shape of a solid circle and a color of white, the bodies of the bacteria each have a shape of a short rod, and the ends of the body are circular-shaped. They often appear in single bodies.<br>2. They are gram-positive bacilli, unlikely to generate spores, free of catalase, oxidase and motility, able to grow in aerobic and anaerobic environments, most suitable to grow at a temperature of 37 ± 1° C.. They |

TABLE 2-continued

Morphologies and General Properties of Lactic Acid Bacteria Strains of the Present Invention

| Strain | Morphology and characteristics |
| --- | --- |
| | belong to a facultative heterofermentative strains and do not generate gas in glucose metabolism. |
| TSR332 strain of *Lactobacillus reuteri* | 1. While TSR332 strain is cultured in the MRS medium, the colonies thereof each have a shape of a solid circle and a color of white, the bodies of the bacteria each have a shape of a short rod, and the ends of the body are circular-shaped. They often appear in single bodies.<br>2. They are gram-positive bacilli, unlikely to generate spores, free of catalase, oxidase and motility, able to grow in aerobic and anaerobic environments, most suitable to grow at a temperature of 37 ± 1° C.. They belong to a facultative heterofermentative strains and do not generate gas in glucose metabolism. |

Example II: Collection, Cultivation and Preservation of Lactic Acid Bacteria Strains The lactic acid bacteria strains collected by the Applicant are preserved in a solution containing 20% glycerol at a temperature of −80° C. Before usage, the strains are activated two times at a temperature of 37° C. for 24 hours with an MRS broth (DIFCO) containing 0.05% cysteine. The lactic acid bacteria strains used in experiments include a TSP05 strain of *Lactobacillus plantarum*, a TSF331 strain of *Lactobacillus fermentum*, and a TSR332 strain of *Lactobacillus reuteri*. The TSP05 strain of *Lactobacillus plantarum* is sourced from pickled vegetables; the TSF331 strain of *Lactobacillus fermentum* and the TSR332 strain of *Lactobacillus reuteri* are sourced from intestines of healthy human beings.

Example III: Animal Experiments of Hepatoprotection Lactic Acid Bacteria Strains CB7B/6N mice are fed with alcohol-containing diet and used in experiments for evaluating the effects of the lactic acid bacteria strains on the alcohol-induced liver tissue damages. The liver function indexes, such as alanine aminotransferase (ALT) and aspartate transaminase (AST) in serum, are measured. Triacylglycerol in livers is also measured to learn the relation of triacylglycerol and fatty livers. Aspartate transaminase (AST) exists in livers, cardiac muscles, muscles, and erythrocytes. Alanine aminotransferase (ALT) mainly exists in hepatocytes. While these cells are necrotized by various factors, transaminases in cells are released to blood. Therefore, while a person suffers hepatitis, myocardial infarction, muscle inflammation or hemolysis, the value of AST may rise. The extent of cellular damage may be evaluated via inspecting the extents of transaminase rising. Similarly, ALT rising is exactly induced by liver inflammation. While livers are damaged by drugs, alcohol, viruses or hypoxia, the extent of hepatocyte damage may be learned via examining the extent of AST or ALT rising in blood tests.

Firstly, 44 C57BL/6N mice are divided in 6 groups, include a control group, an Alcohol group, an "Alcohol+TSP05" group, an "Alcohol+TSF331+TSR332" group, an "Alcohol+TSP05+TSF331+TSR332 ((Alcohol+Mix-LAB)" group, and a "TSP05+TSF331+TSR332 (Mix-LAB)" group. The control group and the Mix-LAB group are fed with LIEBER-DECARLI REGULAR LIQUID DIET CONTROL. The alcohol group and the "alcohol+lactic acid bacteria" groups are fed with LIEBER-DECARLI REGULAR LIQUID DIET ETHANOL. The control group and the Alcohol group are tube-fed with water through gastric tubes two times every day. The "Alcohol+TSP05" group, "Alcohol+TSF331+TSR332" group, "Alcohol+TSP05+TSF331+TSR332 ((Alcohol+Mix-LAB)" group, and "TSP05+TSF331+TSR332 (Mix-LAB)" group are tube-fed with the tested lactic acid bacteria strains. The experiments are undertaken over a span of 4 weeks. Blood are collected every two weeks during the experiments to analyze alanine aminotransferase (ALT), aspartate transaminase (AST), triacylglycerol and total cholesterol. The mice are sacrificed in the fourth week. The liver tissues thereof are taken out for analysis of triacylglycerol, glutathione, glutathione peroxidase, etc.

Glutathione is a very important antioxidant in human bodies, usually called "the mother of all antioxidants". Owing to age, irregular living habit, and poor dietary habit, glutathione may decrease gradually. The concentration of glutathione in the liver indicates the antioxidant ability of a person. Glutathione peroxidase is the generic term of an enzyme group having the activity of peroxidase, functioning to detoxify in organisms and protecting organisms against oxidation. Glutathione peroxidase reduces the peroxides of lipids into corresponding alcohols, reduces free hydrogen peroxide into water, and catalyzes glutathione into the oxidized form thereof.

Analysis of Glutathione (GSH) Concentration

According to the operational manual of the QuantiChrom™ Glutathione Assay Kit, add liver tissue to phosphoric acid buffer solution by a ratio of 1:4, and mix them to form a homogeneous liquid. Take 200 μL of the homogeneous liquid, and use a refrigerated centrifuge to process the homogeneous liquid at a speed of 14000 rpm and a temperature of 4° C. for 10 minutes, and then take out the supernatant liquid ready for test. Next, prepare Blank and Calibrator: add 100 μL ddH$_2$O and 100 μL Calibrator to a 96-well plate, and add 200 μL ddH$_2$O to the Blank and Calibrator wells and mix them uniformly. Take 120 μL Sample and 120 μL Reagent A into a 1.5 mL centrifuge tube, and undertake oscillation mixing. If turbidity appears, centrifugalize the mixture liquid of Sample/Reagent A at a speed of 14000 rpm for 5 minutes. Next, add 200 μL mixture liquid of Sample/Reagent A into the 96-well plate, and add 100 μL Reagent B to the 96-well plate, and then tap the plate to make them mix uniformly. Next, place the plate statically at an ambient temperature for 25 minutes. Next, measure the absorption of OD412 nm by the liquid to work out the concentration of glutathione according to the following formula:

$$GSH(\mu M) = [(OD_{sample} - OD_{Blank})/(OD_{calibrator} - OD_{Blank})] \times 100 \times n$$

wherein $OD_{sample}$ is the light absorption of Sample, $OD_{Blank}$ is the light absorption of Blank, and $OD_{calibrator}$ is the light absorption of Calibrator, and n is the fold of dilution.

Figure 1:
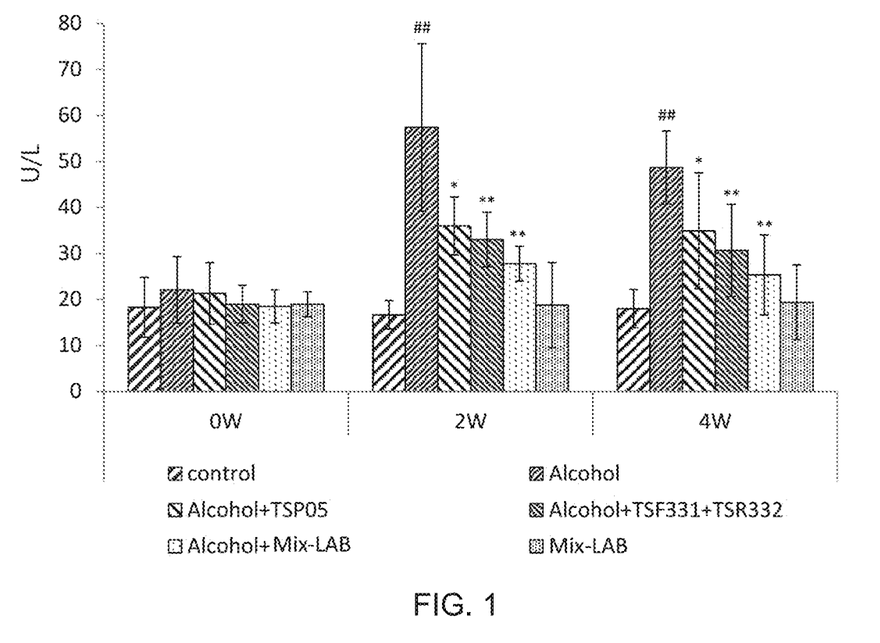

Refer to FIGS. 1-7 for the results of the animal experiments for evaluating the effects of hepatoprotection lactic acid bacteria strains of the present invention. FIG. 1 shows the alanine aminotransferase (ALT) activities in the serum of the six groups of mice in the animal experiments. In the second week (2W) and the fourth week (4W), the Alcohol group is significantly different from the control groups ($p<0.01$). The symbol ## in FIG. 1 indicates that alcohol would raise the liver inflammation index ALT. From FIG. 1, it is learned: feeding the lactic acid bacteria strains of the present invention can obviously lower the ALT value. In FIG. 1, the symbol * and ** denotes the groups, which use alcohol and the lactic acid bacteria strains of the present invention, and which present significant or very significant effect on lowering the rising of the liver inflammation index (the ALT value) induced by alcohol (*, $p<0.05$; **, $p<0.01$). In the second week, the ALT values of the "Alcohol+TSP05" group, the "Alcohol+TSF331+TSR332" group and the "Alcohol+TSP05+TSF331+TSR332" group are respectively 36, 33 and 28 in comparison with the ALT value 57 of the Alcohol group. In the fourth week, the ALT values of the "Alcohol+TSP05" group, the "Alcohol+TSF331+TSR332" group and the "Alcohol+TSP05+TSF331+TSR332" group are respectively 35, 31 and 25 in comparison with the ALT value 49 of the Alcohol group. Therefore, all the three groups fed with the lactic acid bacteria strains of the present invention outperform the Alcohol group significantly in lowering the ALT value, and the "Alcohol+TSP05+TSF331+TSR332" group has the best effect. In the second and fourth weeks, no significant difference exists in the three groups fed with the lactic acid bacteria strains.

Figure 2:
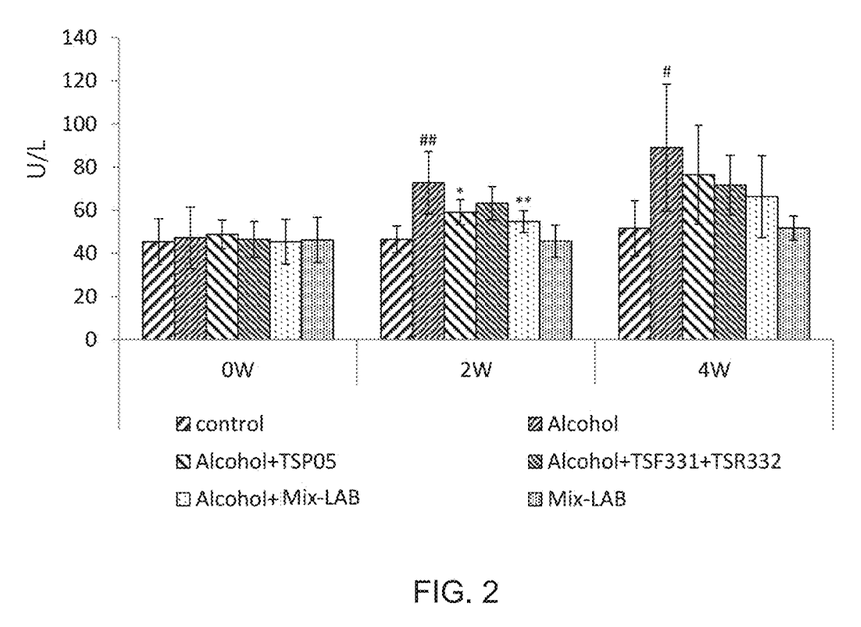

FIG. 2 shows the aspartate transaminase (AST) activities in the serum of the six groups of mice in the animal experiments. It is learned from FIG. 2: the AST value in the serum of the Alcohol group is significantly higher than that of the control group in the second week and the fourth week (##, $p<0.01$; #, $p<0.05$). Therefore, alcohol would raise the liver inflammation index—the AST value. Feeding the lactic acid bacteria strains of the present invention can obviously lower the ALT value. In the second week, the AST value of the "Alcohol+TSP05" group is 59 in comparison with the AST value of 73 of the Alcohol group, and it indicates that TSP05 strain can significantly inhibit the AST rising induced by alcohol (*, $p<0.05$); the AST values of the "Alcohol+TSF331+TSR332" group and the "Alcohol+TSP05+TSF331+TSR332" group are respectively 63 and 54 in comparison with the AST value 73 of the Alcohol group, and it indicates that "TSF331+TSR332" and "TSP05+TSF331+TSR332" can inhibit the AST rising induced by alcohol very significantly (**, $p<0.01$). In the fourth week, the AST values of the "Alcohol+TSP05" group, the "Alcohol+TSF331+TSR332" group and the "Alcohol+TSP05+TSF331+TSR332" group are respectively 76, 72 and 66 in comparison with the AST value 89 of the Alcohol group. Therefore, all the three groups fed with the lactic acid bacteria strains of the present invention outperform the Alcohol group significantly in lowering the AST value, and the "Alcohol+TSP05+TSF331+TSR332" group has the best effect. In the second and fourth weeks, no significant difference exists in the three groups fed with the lactic acid bacteria strains of the present invention.

Figure 3:
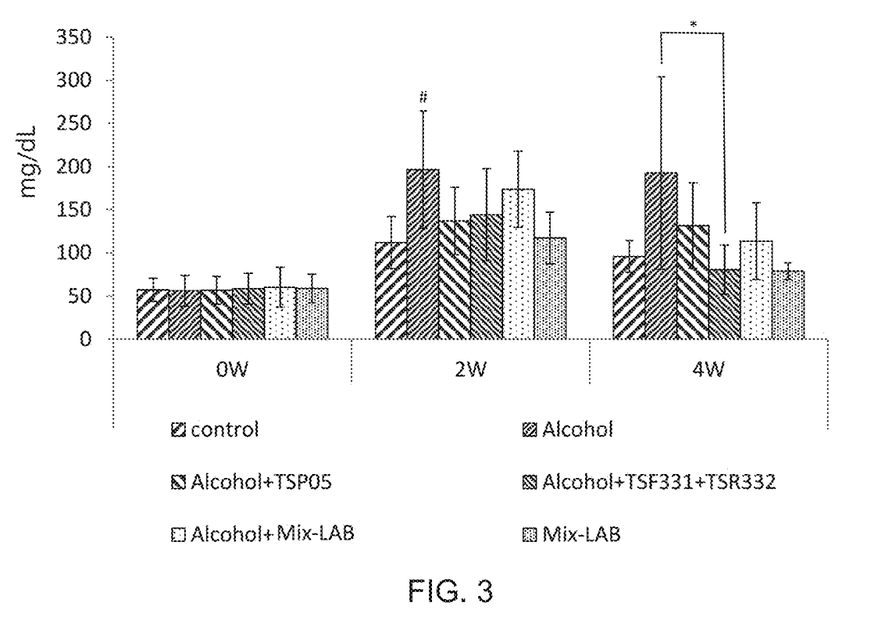

FIG. 3 shows the triacylglycerol concentrations in the serum of the six groups of mice in the animal experiments. The triacylglycerol concentrations of all the six groups are higher in the second week than in the initial stage of the experiment (OW). The triacylglycerol concentration of the Alcohol group is significantly higher than that of the control group in the second week, as indicated by the symbol #in FIG. 3. Although the relationship of the triacylglycerol concentrations of the Alcohol group and the control group in the fourth week is slightly different from that in the second week, it is not obvious ($p=0.08$). All of the "Alcohol+TSP05" group, the "Alcohol+TSF331+TSR332" group and the "Alcohol+TSP05+TSF331+TSR332" group present their effect on lowering triacylglycerol concentration in the second and fourth weeks. Among them, the "Alcohol+TSF331+TSR332" group has better effect on lowering triacylglycerol concentration and presents a significant difference (*, $p<0.05$).

Figure 4:
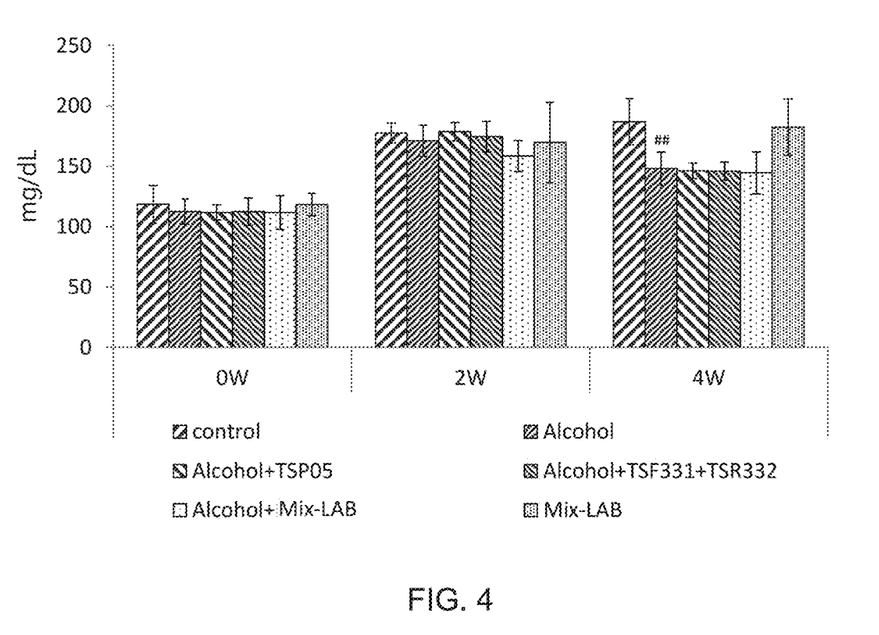

FIG. 4 shows the total cholesterol concentrations in the serum of the six groups of mice in the animal experiments. The total cholesterol concentrations of all the six groups are higher in the second week than in the initial stage of the experiment (OW). No significant difference exists among these groups in the second week. In the fourth, no significant difference exists in the total cholesterol concentrations of the groups fed with alcohol. However, the total cholesterol concentrations of the groups fed with alcohol are lower than that of the groups not fed with alcohol (the control group and the Mix-LAB group). Therefore, the lactic acid bacteria strains of the present invention do not vary the total cholesterol concentrations in the serum within 4 weeks.

Figure 5:
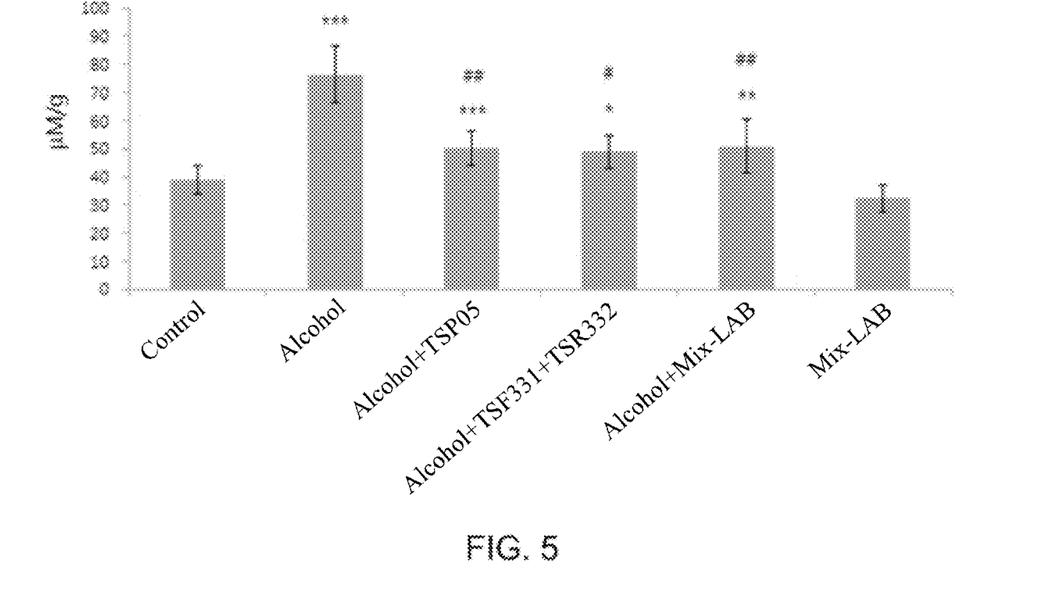
FIG. 5 shows the triacylglycerol concentrations in the livers of the groups of mice fed with the lactic acid bacteria strains of the present invention in the animal experiments, wherein the symbol Alcohol+Mix-LAB represents the mice are fed with LIEBER-DECARLI REGULAR LIQUID DIET ETHANOL and the TSP05 strain of *Lactobacillus plantarum*, the TSF331 strain of *Lactobacillus fermentum* and the TSR332 strain of *Lactobacillus reuteri*; and the symbol Mix-LAB represents the mice are fed with LIEBER-DECARLI REGULAR LIQUID DIET CONTROL and the TSP05 strain of *Lactobacillus plantarum*, the TSF331 strain of *Lactobacillus fermentum* and the TSR332 strain of *Lactobacillus reuteri*.

FIG. 5 shows the triacylglycerol concentrations in the livers of the six groups of mice in the animal experiments, wherein the symbols *, , and * indicate the groups significantly different from the control group, and wherein the symbols #and ##indicate that the groups fed with alcohol and the lactic acid bacteria strains of the present invention are different from the Alcohol group. It is learned from FIG. 5: the triacylglycerol concentrations in the livers of the Alcohol group obviously rises from 39 µM/g to 76 µM/g; the triacylglycerol concentrations in the livers of the "Alcohol+TSP05" group is lowered to 50 µM/g; the triacylglycerol concentrations in the livers of the "Alcohol+TSF331+TSR332" group is lowered to 49 µM/g; the triacylglycerol concentrations in the livers of the "Alcohol+TSP05+TSF331+TSR332" group is lowered to 51 µM/g. Therefore, the triacylglycerol concentrations in the livers of the groups fed with alcohol and the lactic acid bacteria strains of the present invention are significantly lower than that of the Alcohol group. Thus, feeding the lactic acid bacteria strains of the present invention can prevent mice from developing fatty livers. No significant difference exists in the three groups fed with the lactic acid bacteria strains of the present invention.

Figure 6:
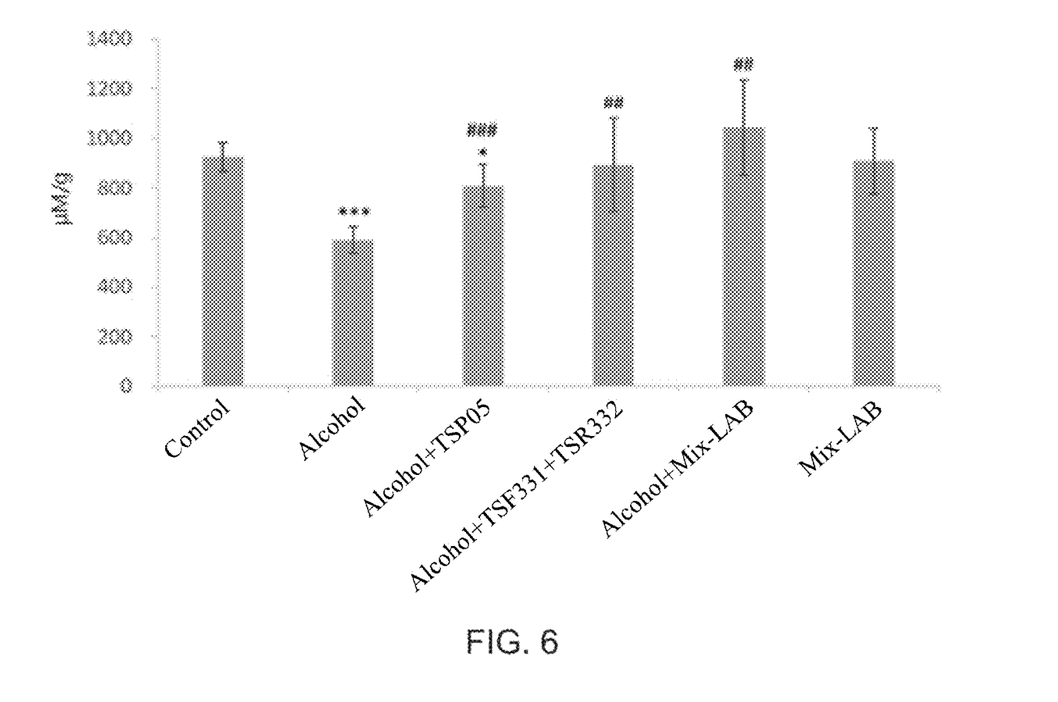
FIG. 6 shows the glutathione concentrations in the livers of the groups of mice fed with the lactic acid bacteria strains of the present invention in animal experiments, wherein the symbol Alcohol+Mix-LAB represents the mice are fed with LIEBER-DECARLI REGULAR LIQUID DIET ETHANOL and the TSP05 strain of *Lactobacillus plantarum*, the TSF331 strain of *Lactobacillus fermentum* and the TSR332 strain of *Lactobacillus reuteri*; and the symbol Mix-LAB represents the mice are fed with LIEBER-DECARLI REGULAR LIQUID DIET CONTROL and the TSP05 strain of *Lactobacillus plantarum*, the TSF331 strain of *Lactobacillus fermentum* and the TSR332 strain of *Lactobacillus reuteri*.

FIG. 6 shows the glutathione concentrations in the livers of the six groups of mice in the animal experiments, wherein the symbols * and *** indicate the groups significantly different from the control group, and wherein ##and ###indicate that the groups fed with alcohol and the lactic acid bacteria strains of the present invention are different from the Alcohol group very significantly. It is learned from FIG. 6: the glutathione concentration in the livers of the Alcohol group is significantly decreased from 925 µM/g to 590 µM/g in comparison with the control group. It indicates that alcohol induces oxidation. The glutathione concentrations in the livers of the groups fed with the lactic acid bacteria strains of the present invention are obviously higher than that of the Alcohol group. The glutathione concentrations are raised in the livers of the groups fed with alcohol and the lactic acid bacteria strains of the present invention. Among them, the "Alcohol+TSP05+TSF331+TSR332" group has better effect on increasing glutathione concentration.

Figure 7:
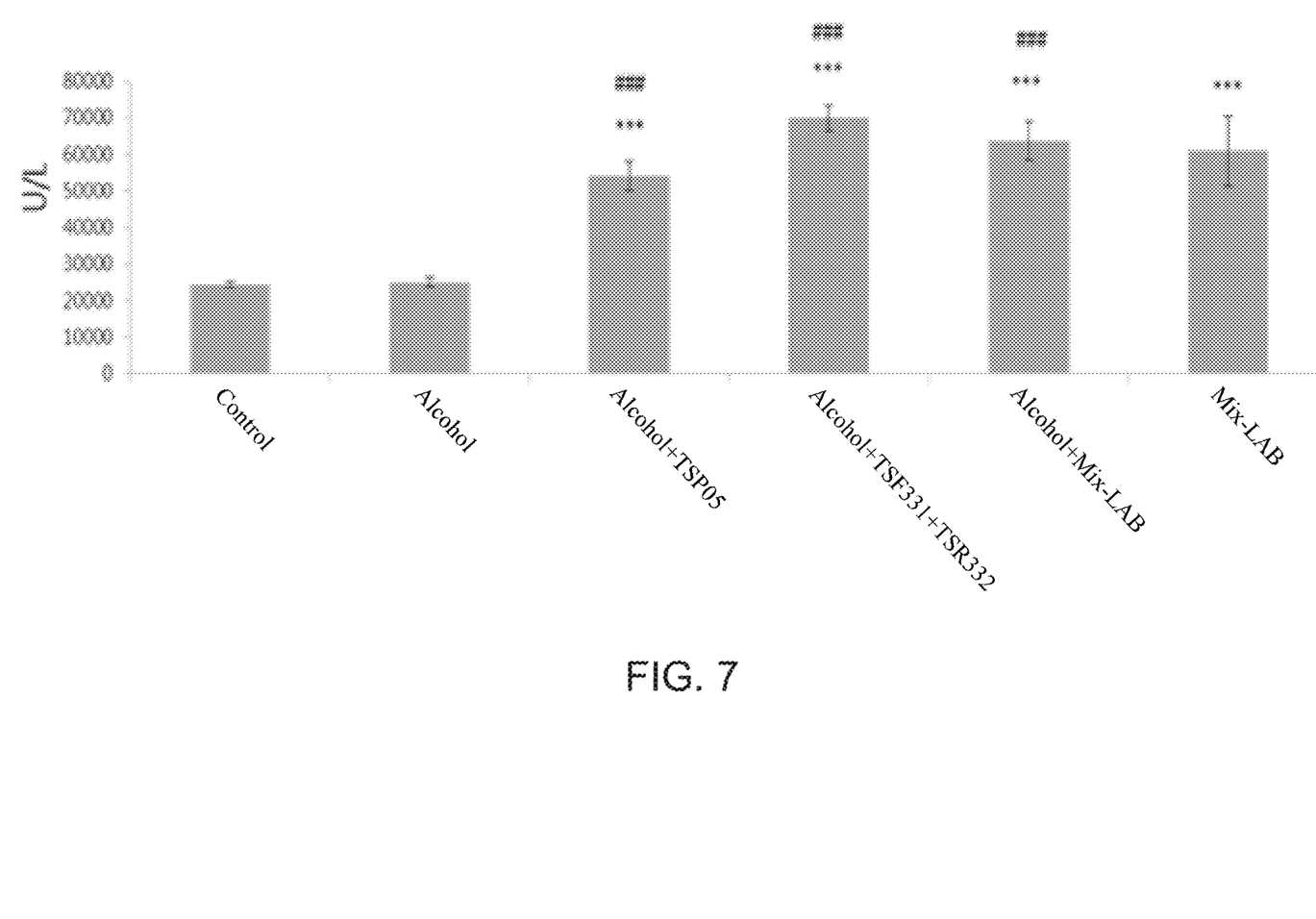
FIG. 7 shows the glutathione peroxidase activities in the livers of the groups of mice fed with the lactic acid bacteria strains of the present invention in animal experiments, wherein the symbol Alcohol+Mix-LAB represents the mice are fed with LIEBER-DECARLI REGULAR LIQUID DIET ETHANOL and the TSP05 strain of *Lactobacillus plantarum*, the TSF331 strain of *Lactobacillus fermentum* and the TSR332 strain of *Lactobacillus reuteri*; and the symbol Mix-LAB represents the mice are fed with LIEBER-DECARLI REGULAR LIQUID DIET CONTROL and the TSP05 strain of *Lactobacillus plantarum*, the TSF331 strain of *Lactobacillus fermentum* and the TSR332 strain of *Lactobacillus reuteri*.

FIG. 7 shows the glutathione peroxidase activities in the livers of the six groups of mice in the animal experiments, wherein the symbol *** indicates the groups different from the control group very significantly, and wherein the symbol ###indicates that the groups fed with alcohol and the lactic acid bacteria strains of the present invention are different from the Alcohol group very significantly. It is learned from FIG. 7: the glutathione peroxidase activity in the livers of the Alcohol group is different from that of the control group insignificantly. Glutathione peroxidase activities in the livers of the groups fed with the lactic acid bacteria strains of the present invention are increased very significantly. Therefore, the lactic acid bacteria strains of the present invention can enhance antioxidant ability.

It is concluded from the abovementioned experiments: the lactic acid bacteria strains-containing food composition and pharmaceutical composition of the present invention can protect livers and prevent from liver inflammation and fatty livers. Further, the present invention can enhance antioxidant ability of livers and protect livers against alcohol-induced oxidation. The hepatoprotection lactic acid bacteria strains of the present invention are free of side effects and thus a new choice for liver protection.

The embodiments have been described above to demonstrate the technical thoughts and characteristics of the present invention to enable the persons skilled in the art to understand, make, and use the present invention. However, these embodiments are only to exemplify the present invention but not to limit the scope of the present invention. Any equivalent modification or variation according to the spirit of the present invention is to be also included within the scope of the present invention.

Bioresource Deposition
CGMCC No. 16710, Institute of Microbiology, Chinese Academy of Sciences, Nov. 5, 2018
CGMCC No. 15527, Institute of Microbiology, Chinese Academy of Sciences, Mar. 29, 2018
CGMCC No. 15528, Institute of Microbiology, Chinese Academy of Sciences, Mar. 29, 2018

What is claimed is:

1. A method for relieving liver damage caused by alcohol, comprising administering a composition to a subject in need thereof to increase a glutathione concentration in a liver of the subject, wherein the composition consists of:
   a TSP05 strain of *Lactobacillus plantarum* deposited in China General Microbiological Culture Collection Center (CGMCC) with a deposition number of CGMCC No. 16710,
   a TSF331 strain of *Lactobacillus fermentum* deposited in China General Microbiological Culture Collection Center with a deposition number of CGMCC No. 15527, and
   a TSR332 strain of *Lactobacillus reuteri* deposited in China General Microbiological Culture Collection Center with a deposition number of CGMCC No. 15528.

2. The method according to claim 1, wherein the TSP05 strain is an active strain, the TSF331 strain is an active strain, and the TSR332 strain is an active strain.

3. The method according to claim 1, wherein the TSP05 strain is an inactivated strain, the TSF331 strain is an inactivated strain, and the TSR332 strain is an inactivated strain.

4. A method for improving decrease in a glutathione concentration in a liver of a subject caused by alcohol comprising administering a composition to the subject to increase the glutathione concentration in the liver of the subject, wherein the composition consists of:
   a TSP05 strain of *Lactobacillus plantarum* deposited in China General Microbiological Culture Collection Center (CGMCC) with a deposition number of CGMCC No. 16710,
   a TSF331 strain of *Lactobacillus fermentum* deposited in China General Microbiological Culture Collection Center with a deposition number of CGMCC No. 15527, and
   a TSR332 strain of *Lactobacillus reuteri* deposited in China General Microbiological Culture Collection Center with a deposition number of CGMCC No. 15528.

5. The method according to claim 4, wherein the TSP05 strain is an active strain, the TSF331 strain is an active strain, and the TSR332 strain is an active strain.

6. The method according to claim 4, wherein the TSP05 strain is an inactivated strain, the TSF331 strain is an inactivated strain, and the TSR332 strain is an inactivated strain.

* * * * *